United States Patent [19]

Chang

[11] Patent Number: 5,929,038
[45] Date of Patent: Jul. 27, 1999

[54] PHARMACEUTICAL PREPARATIONS WHICH INHIBIT HEPATITIS B VIRUS (HBV) REPLICATION

[75] Inventor: Il-Moo Chang, Seoul, Rep. of Korea

[73] Assignee: Choongwae Pharmaceutical Co., Ltd., Seoul, Rep. of Korea

[21] Appl. No.: 08/543,828

[22] Filed: Oct. 16, 1995

Related U.S. Application Data

[63] Continuation of application No. 08/091,449, Jul. 15, 1993, abandoned.

[30] Foreign Application Priority Data

Jul. 15, 1992 [KR] Rep. of Korea .................... 92-12600

[51] Int. Cl.$^6$ ........................... A61K 31/70; A61K 31/35
[52] U.S. Cl. ............................... 514/27; 514/23; 514/25; 514/453; 514/456
[58] Field of Search .................. 514/23, 25, 27, 514/453, 456; 536/18.1

[56] References Cited

U.S. PATENT DOCUMENTS

| | | | |
|---|---|---|---|
| 4,247,698 | 1/1981 | Toyama et al. .......................... | 546/112 |
| 4,410,710 | 10/1983 | Berkowitz et al. ..................... | 549/312 |
| 4,878,921 | 11/1989 | Koga et al. ............................. | 8/646 |
| 5,078,750 | 1/1992 | Komai et al. ............................ | 8/405 |
| 5,145,955 | 9/1992 | Aswal et al. ............................ | 536/124 |

OTHER PUBLICATIONS

Chang et al., Aucubin: Potential Antidote for Alpha–Amanitin Poisoning, *Clinical Toxicology*, 22(1), 77–85 (1984).
Thompson et al., Hematologic Toxicity of AZT . . . , *Fundamental And Applied Toxicology* 17, 159–176 (1991).
John L. Gerin, Ph.D., Antiviral Agents for Hepatitis B, *Hepatology*, vol. 14, No. 1, pp. 198–199 (Jul., 1991).
Korba et al., Hepatocellular Carcinoma in Woodchuck . . . , *Hepatology*, vol. 9, No. 3, pp. 461–470 (1989).
Feldman et al., Ultrastructure of Peripheral Neuropathy . . . , *Laboratory Investigation*, vol. 66, No. 1, pp. 75–85 (1992).
Sells et al., Production of hepatitis B virus particles . . . , *Proc. Natl. Acad. Sci. USA*, vol. 84, pp. 1005–1009, (Feb. 1987).
Korba et al., A cell culture assay for compounds . . . , *Antiviral Research*, 15 (1991) pp. 217–228.
Howard et al., Classification and Taxonomy of Hepatitis Viruses, 1990 International Symposium of Viral Hepatitis and Liver Disease, Section 10: Scientific Workshops, pp. 890–892.
Trim et al., The Preparation and Properties of Aucubin . . . , *Biochem. Journal*, 50, pp. 310–319 (1952).
Chang et al., Aucubin: a New Antidote for Poisonous Amanita Mushrooms, *Phytotherapy Research*, vol. 7, 53–56 (1993).
Chang et al., Protective Activities of Aucubin Against Carbon . . . , *Drug and Chemical Toxicology*, 6(5), 443–453 (1983).
Chang et al., Plants with Liver–Protective Activities . . . , *Advances in Chinese Medicinal Materials Research*, 1985 World Scientific Publ. Co., Singapore, pp. 269–285.
Huh et al., Iridoid Compounds, Korean Journal of *Pharmacognosy*, vol. 16, No. 2, Jun. 1985.
Lee et al., Pharmacology of Iridoid: Antimicrobial Activities of Aucubin, The Second ROK–ROC Symposium on Natural Products Sciences, Dec. 12–16, 1985, Seoul, Korea.

*Primary Examiner*—Elli Peselev
*Attorney, Agent, or Firm*—Birch, Stewart, Kolasch & Birch, LLP

[57] ABSTRACT

On the basis of the present invention in relation with inhibiting hepatitis B virus replication, the pharmaceutical preparations containing the iridoid compounds are represented by the following structural formula(1),

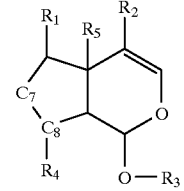

(1)

wherein, R1 is H or OH,
R2 is H or COOR6 (R6 is H or lower alkyl),
R3 is H or β-D-glucose,
R4 is OH, CH$_2$OH or 4-phenylpropionyloxy group,
R5 is H, OH or O-glucose,
C7–C8 shows single bond or double or

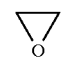

(epoxy bond)

In the above formula, the compound indicates Aucubin, Catapol, Geniposide, Rehmannioside, Harpagoside, Harpagide and Genipin.

Meanwhile, Gardenoside and Swertiamarin such as other iridoids mentioned above are also expected to produce antiviral effect on HBV replication, since they possess the similar chemical structure and other pharmacological characteristics such as liver-protective activities against hepatic damages caused hepatotoxic substances and inhibitory effects on RNA and protein biosyntheses.

The iridoid compounds according to the present invention are characterized by the structure of cyclopenta[C]pyran monoterpenoid, generally found as glycoside in nature. When subjected to β-glucosidase hydrolysis, aglycones are produced, and become biologically effective, exhibiting inhibitory effects on hepatitus B virus replication.

6 Claims, 1 Drawing Sheet

PHARMACEUTICAL PREPARATIONS WHICH INHIBIT HEPATITIS B VIRUS (HBV) REPLICATION

This application is a continuation of application Ser. No. 08/091,449 filed on Jul. 15, 1993, now abandoned.

DESCRIPTION OF THE INVENTION

Figure 1:
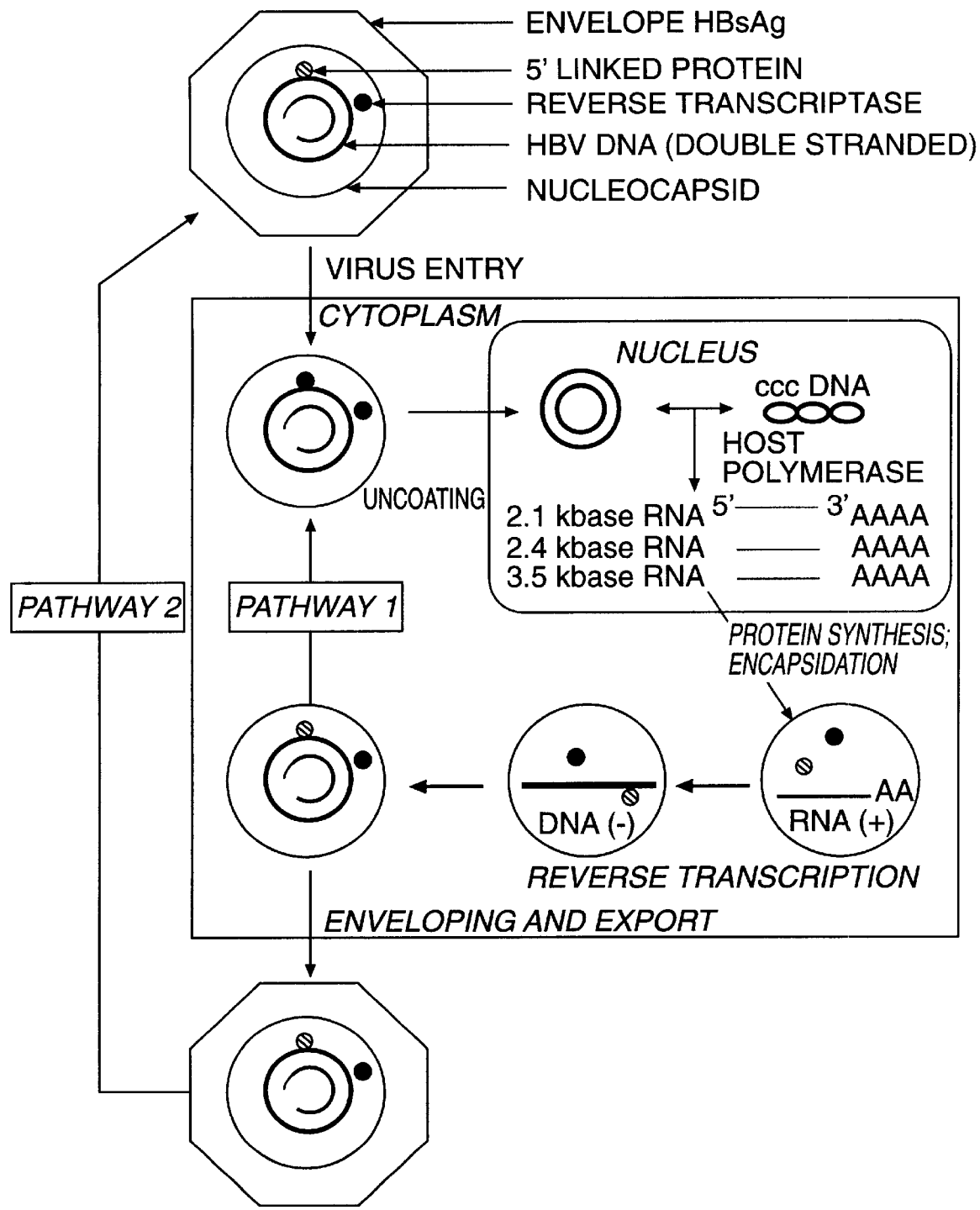
FIG. 1 is a representation of the hepatitis B virus DNA replication in eucaryocytes. Upon infection, virus enters a cell and is transported to the nucleus with uncoating. Viral DNA is converted to ccc DNA that serves as the template for transcription of viral mRNA, including the pregenome. Subsequently pregenomic RNA is reverse transcribed to viral DNA, then recycles through pathway 1 or is secreted as virus particles (pathway 2). This model is excerpted and slightly modified from "Hepadnavirus DNA Synthesis", p. 114 in T. T. Wu, et al. *Viral Hepatitis and Liver Disease,* F. B. Hollinger et al., eds., c. 1991 by Williams and Wilkins, Baltimore, Md. USA.

The invention comprises the iridoid glycosides designated by the following structural formula (1), iridoid aglycones and pharmaceutically accepted salts as effective components for the inhibition of hepatitis B virus DNA replication.

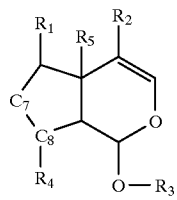
(1)

when, $R_1$ is H or OH, $R_2$ is H or $COOR_6$ (R is H or lower alkyl), $R_3$ is H or β-D-glucose, $R_4$ is OH, $CH_2OH$ or 3-phenylpropionyloxy group, $R_5$ is H, OH, O-glucose or O-glucose (2→1)-glucose, $C_7$–$C_8$ shows single bond or double bond ($\Delta^7$) or

(epoxy bond).

In the formula above, if $R_1$ is OH, $R_2$ is H, $R_3$ is β-D-glucose, $R_4$ is $CH_2OH$, $R_5$ is H, and $C_7$–$C_8$ is double bond, the compound designated by the structural formula(1) indicates Aucubin represented by a structural formula(A), if $R_1$ is OH, $R_2$ is H, $R_3$ is β-D-glucose, $R_4$ is $CH_2OH$, $R_5$ is H, and $C_7$–$C_8$ is epoxy, the compound designated by the structural formula(1) indicates Catalpol represented by a structural formula(B), if $R_1$ is H, $R_2$ is $COOR_6$($R_6$ is $CH_3$), $R_3$ is β-D-glucose, $R_4$ is $C_2OH$, $R_5$ is H, and $C_7$–$C_8$ is double bond, the compound designated by the structural formula(1) indicates Geniposide represented by a structural formula(C), if $R_1$ is OH, $R_2$ is H, $R_3$ is β-D-glucose, $R_4$ is $CH_2OH$, $R_5$ is O-glucose-(2→1)-glucose and $C_7$–$C_8$ is double bond, the compound designated by the structural formula(1) indicates Rehmannioside represented by a structural formula(D), if $R_1$ is OH, $R_2$ is H, $R_3$ is β-D-glucose, $R_4$ is 3-phenylpropionyloxy group, $R_5$ is OH, and $C_7$–$C_8$ is single bond, the compound designated by the structural formula(1) indicates Harpagoside represented by a structural formula (E), if $R_1$ is OH, $R_2$ is H, $R_3$ is β-D-glucose, $R_4$ is OH, $R_5$ is OH, and $C_7$–$C_8$ is single bond, the compound designated by the structural formula(1) indicates Harpagide represented by a structural formula(F), if $R_1$ is H, $R_2$ is $COOR_6$($R_6$ is $CH_3$), $R_3$ is H, $R_4$ is $CH_2OH$, $R_5$ is H, and $C_7$–$C_8$ is double bond, the compound designated by the structural formula(1) indicates Genipin represented by a structural formula(G).

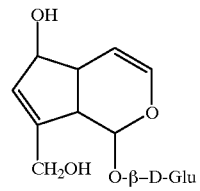
(A)

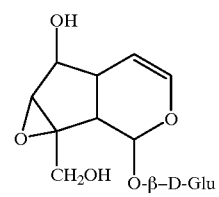
(B)

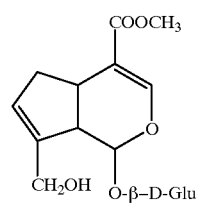
(C)

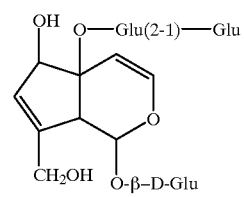
(D)

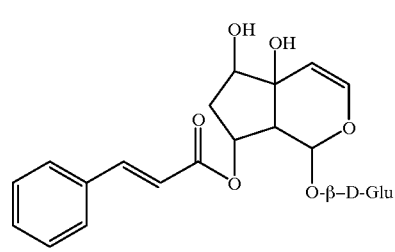
(E)

(F)
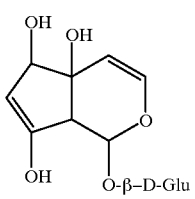

(G)

Also, Gardenoside designated by a structural formula(II) and Swertiamarin designated by a structural formula(I) belong to a group of iridoid compounds. These compounds exhibit similar chemical and pharmacological characteristics of other iridoid compounds such as Aucubin that exhibits liver-protective activities and exerts an antiviral activity aganist HBV infection. Therefore, they are included in present report for the submission of patent by inventor.

(H)
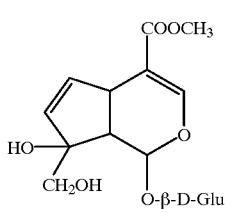

(I)
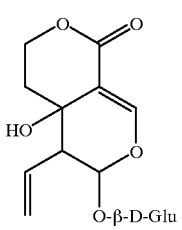

Iridoids represent a group of monoterpenoid compounds and are found usually as glycosides in nature. When they are subjected to enzymatic hydrolysis by the sugar hydrolyzing enzyme such as β-glucosidase, a glucose molecule and aglucone are formed as the hydrolyzed products. The aglucone (genin) form is easily converted to its dialdehyde products and it can proceed further polymerization as shown in following scheme.

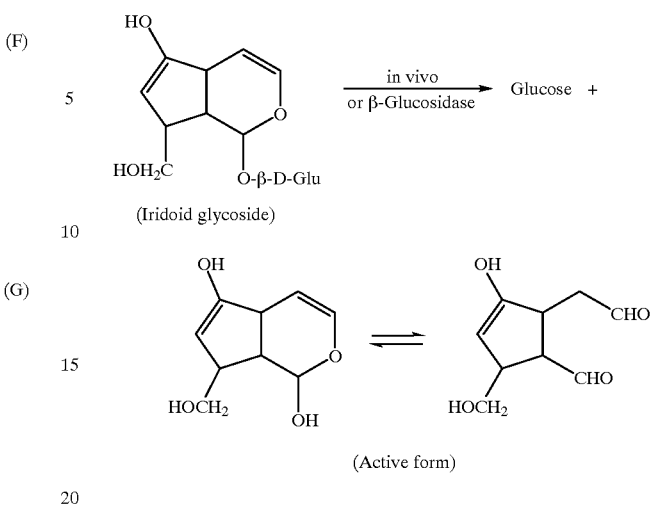

It has been recognized that the aglucone formation is a prerequisite step to exhibit such biological activities of iridoid compounds as inhibitory effects on RNA and protein biosynthesis, reported earlier in a publication entitled in "Effects of Iridoid Compounds on RNA and Protein Biosynthesis in Sarcoma 180 cells" appearing in the Korean Journal of Pharmacognosy, 16, 99,(1985) by S. O. Huh, et al.

Leaves of Aucuba japonica(Cornaceae) are a major source for Aucubin, an iridoid compound. The chemical sturucture of Aucubin (1, 4, 5, 7α-tetrahydro-5-hydroxy-17-(hydroxymethyl)cyclopenta[c]pyran-1-yl-β-D-glucopyranose) was first reported by R. Trim and R. Hill, Biochem. J. 50, 310(1952).

Also, the compound has been reported by the present inventor (I. M. Chang, H. S. Yun(Choi), In Advances in Chinese Medicinal Materials Research (ed. H. M. Chang et al.), World Scientific Publishing Company, Singapore, p. 269 (1985).

Important biological activities of the compound reported previously by the inventor are summarized as follows;

1) Antibacterial activity
   Antibacterial activity was noted mainly on gram positive bacteria (I. M. Chang et al, in Proceedings, the 2nd ROK-ROC symposium on Natural Products Sciences p.94, (1985) (Seoul National University Press).

2) Liver-protective activities
   Experiments done on laboratory animals show that the iridoid compounds including Aucubin protect the liver from hepatic damage induced by carbon tetrachloride intoxication (I. M. Chang et al., Drug Chem. Toxicol., 6, 443, (1983). Aucubin also protects the liver from damages caused by α-amantin intoxication in mice (I. M. Chang et al., Clinical Toxicol., 22, 77 (1984)).

3) Inhibitory effects on RNA and protein biosynthesis
   Iridoid compounds including Aucubin can exert inhibitory effects on RNA and protein biosynthesis in Sarcoma 180 cells (I. M. Chang et al, Korean Journal of Pharmacognosy, 16, 99 (1985), and I. M. Chang and H. S. Yun, in Advances in Chinese Medicinal Materials Research (ed. H. M. Chang et al.), Singapore. p. 269 (1985)).

4) Detoxification activity
   Aucubin detoxifies toxic Amanita mushrooms' poisoning (Korean Patent Publication No. 92-2290, by the present inventor).

Aucubin showed potent antidotal activity in beagle dogs intoxicated by toxic mushroom extracts (I. M. Chang and Y. Yamaura, Phytotherapy Res., 7, 53 (1993)).

HBV belongs to the genus of hepadnavirus in the hepadnaviridae family. The genome of HBV consists of d-s DNA (covalently closed circular DNA), and the virion is essentially spherical, being 42 nm across. The host range for infection includes chimpanzee, gibbon, gorilla, woodchuck, and human (C. R. Howard and J. L. Melnick, "Classification and Taxonomy of Hepatitis Viruses", in *Proceedings of International Symposium on Viral Hepatitis and Liver Disease,* (ed. F. B. Hollinger et al.) Williams and Wilkins, Baltimore, p. 890 (1990) Although HBV is a DNA virus, it requires reverse transcription for replication through the formation of a (+) strand RNA intermediate. A summary of HBV DNA, replication is shown in FIG. 1.

Hepatitis B caused by HBV infection in humans is a major health problem throughout the world. It not only causes acute and chronic hepatitis, but also contributes to formation of hepatocellular carcinoma. In this regard, great efforts have been made to develop clinically useful therapeutics for hepatitis B. For example, interferon and several nucleoside analogs reported as antiviral agents have shown relatively low cure rate of hepatitis B in humans, and they have often produced serous adverse effects. In the case of 2',3'-dideoxycytidine (ddC), a newly developed nucleoside analog, the clinical efficacy for the treatment of hepatitis B has been claimed due to high toxicity on the central and peripheral nervous system (Feldman et al., Lab. Invest., 66(I), 75(1992), and toxicity on hematopoietic cells (Thompson et al., Fund.-Appl. Toxicol. 17, 159(1991). Another nucleoside analog, ara-AMP which has been used clinically for long time, was found to transiently suppress HBV infection, revealing often serious toxicities. So long-term therapy using ara-AMP should be avoided (J. L. Gerin, Hepatology, 14, 198 (1991).

Aiming for developing a new antiviral therapeutics for hepatitis B infection, the present inventor has studied several iridoid compounds (structural formulae A to I) derived from medicinal plants as stated in preceeding pages, since those iridoid compounds were found to exhibit liver-protective activites against hepatotoxic chemicals such as $CCl_4$ and α-amanitin, and possess biological activity as inhibitors of RNA synthesis and protein synthesis.

In order to evaluate potential antiviral activities of iridoid compounds with respect to their biological characterastics such as the inhibitory effects on RNA and protein biosynthesis, an in vitro cell culture system using 2. 2. 15 cells (Hep G2 cells) was chosen (M. A. Sells et al., Proc. Natl. Acad. Sci. (U.S.A.), i, 1005 (1987). The methodology for assaying antiviral activities using this cell line was employed as reported elsewhere (B. E. Korba and G. Milman; A cell culture assay for compounds which inhibit hepatitis B virus replication, Antiviral Research, 15, 217 (1991).

Iridoid glycosides which exert such pharmacological activities as stated above were discovered to be very effective natural products for the inhibition of HBV DNA replication and found to be useful materials as potential therapeutics with relatively low cytotoxicity and acute toxicities for the treatment of hepatitis caused by HBV infection (Table 1–3). In the case where an iridoid glycoside was pretreated with β-glycosidase and added to 2. 2. 15 cell infected with HBV DNA, the replication of HBV DNA was significantly suppressed. When β-glucosidase alone was used for treatment, without the addition of the iridoid glycosides, no inhibition occurred. Therefore, the production of iridoid aglycone (genin form) from the glycoside by sugar hydrolyzing enzyme was a prerequisite process to exert antiviral activities as noted previously.

As the results show, Aucubin produces a marked inhibition of HBV DNA biosynthesis. Taking an advantage of low level of toxicity, and abundant plant resources for the production of the compounds, the present invention of developing a new antiviral agents for the treatment of hepatitis B infection can be verified by the following examples.

Evaluation of antiviral activities of Aucubin using 2. 2. 15 cell culture was conducted as follows;

EXAMPLE 1

Effects of Aucubin on the Inhibition of Hepatitus B Virus Replication

Details of the assay methodology can be found in the report of Korba and Milman (Antiviral Res., 15, 217(1991). Briefly, the procedures of experiments are described.

1) Cell culture

The antiviral evaluation was performed on two separate passages of cells (2. 2. 15 cell). All wells of all microplates were seeded at the same density and at the same time. The cell line was maintained in RPMI 1640 culture medium containg 5% of fetal bovine serum (FBS), 2 $\mu$M glutamine and 50 $\mu$g/ml gentamicin sulfate. The cell culture was examined for resistance to G418 for mycoplasma contamination. Cells ($1 \times 10^4/cm^2$) were placed into a multi-well culture plate (96 wells) and cultured for seven days to confluence and further kept for two to three days in confluent condition to stabilize HBV DNA level. Then culture medium was replaced 24 hours before cells were exposed to test samples. During the nine day period, culture medium was replaced and the iridoid samples were added to the cultures in fresh culture medium at 24 hour intervals. Immediately before the first dose of test compound (Day 0), and after 3, 6, and 9 days treatment, culture medium was collected and stored at −70° C. before viral DNA analysis. Then the cells were prepared to measure the contents of intracellular HBV DNA.

2) Extraction of DNA and RNA

To measure the content of extracellular HBV DNA, a 0.2 ml portion of culture medium was incubated for 20 min. at 25° C. in 1 M NaOH/10×SSC (1×SSC=0.15 M NaCl/0.015 M sodium citrate, pH 7.2) and applied to a nitrocellulose membrane presoaked in 20×SSC by using a slot blot apparatus. Samples were washed two times in 0.5 ml of 1 M Tris/2 M NaCl (pH 7.2) and one time in 0.5 ml of 20×SSC. Then, membrane filters were washed in 2×SSC and heated at 80° C. for 1 hour under vacuum.

To analyze intracellular HBV DNA, cells were dissolved in 0.5 ml of lysis buffer (4 M of guanidine isothiocyanate, 7% of 2-mercaptoethanol and 2% sarkosil) per well and dialyzed for 1 hour against 6 L of 50 $\mu$M Tris, pH 8.0–1 $\mu$M NaEDTA using a microdialyzer. Lysates were then digested with proteinase K, extracted with phenol and chloroform, precipitated with ethanol, and resuspended in 10 $\mu$M Tris pH 8.0–1.0 $\mu$M NaEDTA. Cultured cells maintained in a 10 cm dish were dissolved in 6 ml of lysis buffer and cellular RNA and DNA were prepared by the method of Korba et al. (Hepatology, 9, 461 (1989)).

3) Gel electrophoresis

Cellular DNA samples (10 $\mu$g/lane) were digested with Hind III enzyme electrophoresis on a 1% agarose gel, and transfered to a nitrocellulose membrane. Unfractionated cellular RNA (30 μg/lane) was denatured, and electrophoresed or a 1% agarose gel containing 6% formaldehyde/NaPO$_4$(pH 6.5), and transferred to a nitrocellulose membrane.

4) Hybridization analysis of hepatitis B virus DNA

A purified 3.2 kb EcoRI HBV DNA fragment labeled by nick translation with |$^{32}$P|dCTP was used as a hybridization probe. Conditions for hybridization and post-washing were according to the method of Korba et al. (Hematology, 9, 461 (1989). The amount of HBV nucleic acids was measured by using an Ambis beta scanner. The relative amounts of radioactivities of $^{32}$P hybridized was compared to known amounts of HBV DNA standard applied to each nitrocellulose membrane filter (gel or slot blot). A standard curve was used to correlate relative radioactivies with HBV DNA quantities.

Due to the inherent variations in the amounts of both intracellular and extracellular HBV DNA, only inhibition greater than 3.5-fold (for HBV virion DNA) or 3.0-fold (for replication intermediates, RI in Table I) from the average levels for the HBV DNA forms in untreated cells are considered to be statistically significant (P<0.05) in present experiments. The levels of integrated HBV DNA in each cellular DNA preparation (which remains constant on a per cell basis in present experiments) were used to calculate the levels of intracellular HBV DNA forms, thereby eliminating technical variations inherent in the blot hybridization analysis. Typical values for extracellular HBV virion DNA in untreated cells range from 50 to 1150 pg/ml culture medium (average of about 76 pg/ml). Intracellular HBV DNA replication intermediates (RI) in untreated cells range from 50 to 100 pg/ug cell DNA (average about 74 pg/μg cell DNA). In general, inhibitions in the levels of intracellular HBV due to treatment with antiviral agents are less profound, and occur more slowly than suppressions in the levels of HBV virion DNA.

On the basis of the results from the hybridization analysis performed, 1.0 pg intracellular HBV DNA/jig cellular DNA corresponded to 2–3, genomic copies per cell and 1.0 pg of extracellular HBV DNA/ml culture medium to 3×10$^5$ viral particles/ml.

Results

TABLE 1

Effects of Aucubin on HBV DNA replication in 2.2 15 cells in culture.

| Exp. No. | Treatment | Intracellular HBV DNA* (pg/μg cell DNA) | | HBV Virion DNA** (pg/ml culture medium) | | | |
|---|---|---|---|---|---|---|---|
| | | Mono. | RI[1] | Day 0 | Day 3 | Day 6 | Day 9 |
| 118AA | (Untreated cells) | 2.8 | 78 | 61 | 83 | 110 | 110 |
| 118AB | | 2.9 | 73 | 70 | 55 | 85 | 81 |
| 118BA | | 2.5 | 56 | 88 | 100 | 92 | 88 |
| 118BB | | 2.4 | 69 | 69 | 64 | 52 | 74 |
| 118AE | ddC 25 μM[2] | 1.1 | 1 | 65 | 41 | 15 | 0.3 |
| 118AF | | 1.2 | 1 | 70 | 33 | 13 | 0.0 |
| 118BE | | 0.8 | 1 | 78 | 31 | 10 | 0.0 |
| 118BF | | 1.0 | 1 | 60 | 40 | 12 | 0.0 |
| 123AA | Aucubin, 1000 μM + Gly.[3] | 2.2 | 3 | 64 | 84 | 25 | 1 |
| 123AB | | 2.1 | 2 | 81 | 79 | 18 | 1 |
| 123BA | | 2.3 | 3 | 69 | 70 | 22 | 1 |
| 123BB | | 2.6 | 2 | 80 | 67 | 20 | 1 |
| 123AC | Aucubin, 300 μM + Gly. | 2.0 | 7 | 54 | 66 | 54 | 9 |
| 123AD | | 2.0 | 6 | 59 | 89 | 48 | 7 |
| 123BC | | 2.4 | 5 | 77 | 98 | 44 | 5 |
| 123BD | | 2.5 | 9 | 66 | 84 | 51 | 6 |
| 123AE | Aucubin, 30 μM + Gly. | 2.6 | 21 | 52 | 59 | 40 | 15 |
| 123AF | | 2.8 | 27 | 76 | 77 | 48 | 22 |
| 123BE | | 2.4 | 22 | 55 | 79 | 66 | 20 |
| 123BF | | 2.1 | 26 | 62 | 51 | 59 | 17 |
| 123AG | Aucubin, 30 μM + Gly. | 2.6 | 70 | 62 | 94 | 49 | 55 |
| 123AH | | 2.8 | 75 | 67 | 82 | 58 | 72 |
| 123BG | | 2.4 | 63 | 69 | 97 | 61 | 70 |
| 123BH | | 2.1 | 68 | 71 | 62 | 69 | 67 |
| 123AI | Aucubin, 1000 μM + 30'Gly.[4] | 2.3 | 3 | 84 | 67 | 20 | 2 |
| 123AJ | | 2.0 | 2 | 70 | 79 | 17 | 2 |
| 123BI | | 2.0 | 4 | 79 | 66 | 16 | 2 |
| 123BJ | | 2.1 | 4 | 59 | 78 | 24 | 3 |
| 123AK | Aucubin, 300 μM + 30'Gly. | 2.4 | 11 | 88 | 80 | 54 | 9 |
| 123AL | | 2.6 | 10 | 51 | 55 | 39 | 7 |
| 123BK | | 1.9 | 7 | 50 | 54 | 44 | 6 |
| 123BL | | 2.0 | 9 | 59 | 61 | 49 | 8 |
| 123AM | Aucubin, 100 μM + 30'Gly. | 2.5 | 33 | 55 | 80 | 50 | 20 |
| 123AN | | 2.4 | 32 | 51 | 49 | 66 | 17 |
| 123BM | | 2.3 | 27 | 69 | 50 | 41 | 16 |
| 123BN | | 2.7 | 26 | 86 | 57 | 45 | 21 |

TABLE 1-continued

Effects of Aucubin on HBV DNA replication in 2.2 15 cells in culture.

| Exp. No. | Treatment | Intracellular HBV DNA* (pg/μg cell DNA) | | HBV Virion DNA** (pg/ml culture medium) | | | |
|---|---|---|---|---|---|---|---|
| | | Mono. | RI[1] | Day 0 | Day 3 | Day 6 | Day 9 |
| 123AN | Aucubin, 30 μM + 30'Gly. | 2.5 | 92 | 57 | 85 | 70 | 80 |
| 123AO | | 2.4 | 68 | 61 | 94 | 62 | 48 |
| 123BN | | 2.3 | 59 | 79 | 51 | 55 | 87 |
| 123BO | | 2.7 | 68 | 68 | 75 | 75 | 91 |

*Analysis of intracellular HBV DNA was carried out 24 hrs following the 9th day of treatment.
[1]RI: Replicating Intermediate.
**Sensitivity cut-off for virion HBV DNA was 0.1 pg/ml.
[2]ddC: 2',3',-dideoxycytidine, a positive control as known antiviral agent.
[3]GLY.: Aucubin was mixed with β-glucosidase as follows, but no incubation was performed before the addition of culture cell.
[4]30'GLY.: Aucubin was incubated in the presence of 2.5 mg/ml β-glycosidase at 37° C. in 0.1M sodium acetate(pH 5) for 30 min before it was added to culture medium. The stock solution was diluted 100- fold and the final β-glycosidase concentration in the culture medium was 25 mg/ml.

As shown in the above experiment, iridoid compounds according to the present invention produced a potent inhibition of HBV DNA replication Therefore, drugs prepared according to the invention can be used for the prevention and treatment of hepatitis caused by hepatitis B virus.

EXAMPLE 2

Cell toxicity test

Toxicity testing was performed in 96-well flat bottomed tissue culture plates. These cells were cultured and treated on same schedule as the test compounds used for antiviral evaluation (example 1). Each group at four concentrations was tested in triplicate cultures. Uptake of neutral red dye was used to determine the relative level of toxicity. The absorbance of internalized dye at 510 nm ($A_{510}$) was used for the quantitative analysis. Values are presented as a percentage of the average $A_{510}$ values (mean ± standard deviation) in 9 separate cultures of untreated cells maintained on the same 96-well plate as used for the test compound. The percentage of dye uptake in the 9 controlled cultures on plate 23 was 100±4. Results showed no significant cell toxicity in the range of concentration of the test compound.

TABLE 2

Cell toxicity test

| | | Amount of dye uptake by concentrations (% of control) | | | |
|---|---|---|---|---|---|
| Plate | Treatments | 10,000 μM | 3000 μM | 1000 μM | 300 μM |
| 23 | Aucubin | 45 ± 3 | 85 ± 3 | 100 ± 1 | 99 ± 1 |
| 23 | Aucubin + 30'GLY.* | 67 ± 3 | 82 ± 2 | 99 ± 2 | 99 ± 2 |
| 23 | Aucubin + GLY.** | 63 ± 6 | 93 ± 5 | 99 ± 1 | 99 ± 2 |
| 23 | GLY.only*** | 75 ± 2 | 82 ± 2 | 99 ± 5 | 100 ± 2 |

*30'GLY.: Aucubin was preincubated with β-glucosidase for 30 min at 37° C. in 0.1M sodium acetate (pH 5) before it was added to a culture medium. (The stoke solution was diluted 100-fold and the final β-glucosidase concentration in the culture medium was 25 mg/ml.)
**GLY.: Aucubin was mixed as mentioned above without preincubation of the β-glucosidase
***GLY.only : β-glucosidase only treated without addition of Aucubin.

EXAMPLE 3

Acute toxicity test in mice

To examine possible acute toxicity of aucubin, a single dose of 100, 300, 600 and 900 mg/kg was administered intraperitoneally to each mouse and the fatality rate was investigated during twenty-four hour period.

TABLE 3

Acute toxicity test in mice.

| Treated Material | Dose* (mg/kg) | Fatalities (No.) | SGOT (IU/L) | Alkaline phosphatase (IU/L) | Triglyceride (mg/dL) |
|---|---|---|---|---|---|
| Aucubin | 100 | 0 | 261 | 236 | |
| | 300 | 0 | 194 | 157 | 35 |
| | 600 | 0 | 179 | 135 | 39 |
| | 900 | 0 | 162 | | 51 |

*Each dosaged group consisted of ten mice.
Serum was collected at 24 hours after treaments of Aucubin.

Results in Table 3 showed no fatality, implying the minimum fatal dose was more than 900 mg/kg. In the case where a high dose was administered, activities of SGOT and alkaline phosphatase showed a slight decline and triglyceride contents elevated slightly, indicating that no serious toxic effect occurred.

The iridoid compounds according to the present invention, formulated as pharmaceutical preparations, can be orally and parenterally administered. This process is done by mixing with a vehicle or other typical formulation. This pratice is generally used in the pharmaceutical manufacturing field.

The following are examples of preparations according to the present invention:

Preparation 1 (tablet)

| Aucubin (per tablet) | 500 mg |
|---|---|
| Lactose | 80 mg |
| Sucrose | 80 mg |
| Acacia rubber | 10 mg |
| Talc | 10 mg |
| Magnesium stearate | 1 mg |
| Purified water | Proper amount |

Aucubin, lactose, sucrose and acacia rubber were mixed and proper amount of water was added and then boiled down. Granules were made by passing through a sieve. Then, the humid granules were desicated at 40° C., and small pieces of granules were produced by passing them through a No. 1 sieve, then talc and magnesium stearate were added, and tableted.

Preparation 2) (capsuled)

| Geniposide | 500 mg |
|---|---|
| Lactose | 80 mg |
| Magnesium stearate | proper amount |

These components were mixed and filled in hard capsules.

Preparation 3 (injection)

50 mg of Aucubin was dissolved in 5 ml of sterilized physiological saline solution heated at 60° C., filled in a aseptic vial, and sealed.

What is claimed:

1. A method for treating hepatitis B viral infection which comprises administering to a patient an amount effective for inhibiting hepatitis B virus replication of a composition comprising an iridoid compound of the formula (1), or a pharmaceutically acceptable salt thereof:

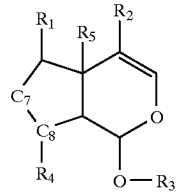

(1)

wherein $R_1$ is H or OH,
$R_2$ is H or $COOR_6$, wherein $R_6$ is H or lower alkyl;
$R_3$ is H or β-D-glucose;
$R_4$ is OH, $CH_2OH$ or 3-phenylpropionyloxy-;
$R_5$ is H, OH, O-glucose or O-glucose-(2→1)-glucose; and
$C_7$ and $C_8$ are joined by a single bond or a double bond
and a pharmaceutically acceptable excipient or adjuvant.

2. The method of claim 1, wherein said iridoid compound is Aucubin.

3. The method of claim 1, wherein said iridoid compound is Geniposide.

4. The method of claim 1, wherein said iridoid compound is Rehmannoside.

5. The method of claim 1, wherein said iridoid compound is Harpagoside.

6. The method of claim 1, wherein said iridoid compound is Harpagide.

* * * * *